United States Patent [19]
Bardy et al.

[11] Patent Number: 5,231,996
[45] Date of Patent: Aug. 3, 1993

[54] REMOVABLE ENDOCARDIAL LEAD

[75] Inventors: Gust H. Bardy, Seattle, Wash.; Norbert H. Cannon, Shoreview, Minn.; Arnold W. Thornton, Roseville, Minn.; Terrell W. Williams, Coon Rapids, Minn.

[73] Assignee: Medtronic, Inc., Minneapolis, Minn.

[21] Appl. No.: 827,121

[22] Filed: Jan. 28, 1992

[51] Int. Cl.⁵ .................................... A61N 1/05
[52] U.S. Cl. ............................ 128/785; 128/786; 606/108
[58] Field of Search ............... 128/783, 784, 785, 786, 128/642, 419 P; 606/1, 106, 108

[56] References Cited

U.S. PATENT DOCUMENTS

| | | | |
|---|---|---|---|
| 3,572,344 | 3/1971 | Bolduc | 128/418 |
| 3,788,329 | 1/1974 | Friedman | 128/418 |
| 3,844,292 | 10/1974 | Bolduc | 128/418 |
| 3,902,501 | 9/1975 | Citron et al. | 128/418 |
| 3,974,834 | 8/1976 | Kane | 128/418 |
| 4,209,019 | 6/1980 | Dutcher et al. | 128/419 |
| 4,437,475 | 3/1984 | White | 128/785 |
| 4,502,492 | 3/1985 | Bornzin | 128/785 |
| 4,572,605 | 2/1986 | Hess | 339/177 |
| 4,574,800 | 3/1986 | Peers-Trevarton | 128/303 |
| 4,582,056 | 4/1986 | McCorkle, Jr. | 128/303 |
| 4,660,571 | 4/1987 | Hess et al. | 128/784 |
| 4,920,980 | 5/1990 | Jackowski | 128/786 |
| 4,944,088 | 7/1990 | Doan et al. | 29/858 |
| 4,988,347 | 1/1991 | Goode et al. | 606/1 |
| 5,170,803 | 12/1992 | Hewson et al. | 128/786 |

OTHER PUBLICATIONS

Bilgutay et al., "Incarceration of transvenous pacemaker electrode. Removal by traction", American Heart Journal, vol. 77, 1969, pp. 377–379.

Foster et al., "Percutaneous removal of ventricular pacemaker electrodes using a Dormier basket", International Journal Of Cardiology, 21 (1988) 127–134.

Primary Examiner—Kyle L. Howell
Assistant Examiner—Kennedy J. Schaetzle
Attorney, Agent, or Firm—John A. Rissman; Harold R. Patton

[57] ABSTRACT

In a coiled wire medical lead structure, such as a transvenous, endocardial cardiac pacemaker and/or cardioverter/defibrillator lead, an improved mechanical structure for strengthening the lead to enable its intact removal by traction after a period of chronic implant, one or more normally relaxed, nonextensible filaments loosely contained within the insulating sheath and having proximal and distal ends mechanically coupled to the connector and electrode shank, respectively, of the lead operate as means for restraining the stretching of the lead body to a stretched length exceeding the relaxed, predetermined length by an amount sufficient to allow the lead to be stretched without breaking in its normal usage and during removal by traction. In certain embodiments, the filament may take the form of a loosely woven fabric sheath formed in a tubular shape and fitted in the space between the lead body outer sheath and one or more coiled wire conductors. The filament(s) or woven sheath may be embedded within or on the interior surface of the outer insulating sheath or an inner insulating sheath of a bipolar or multipolar lead.

10 Claims, 5 Drawing Sheets

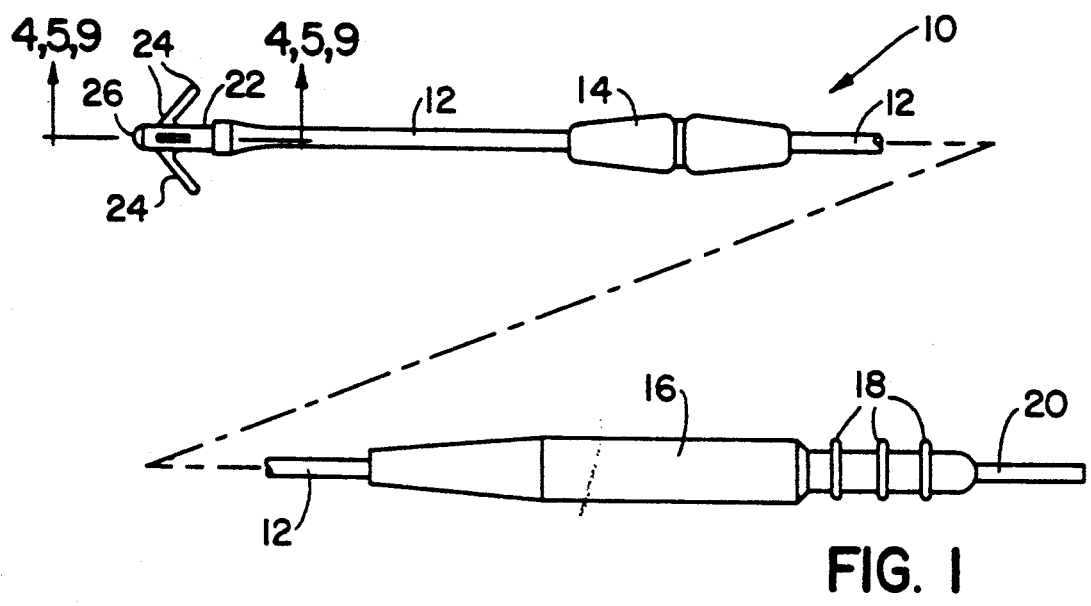
FIG. 1
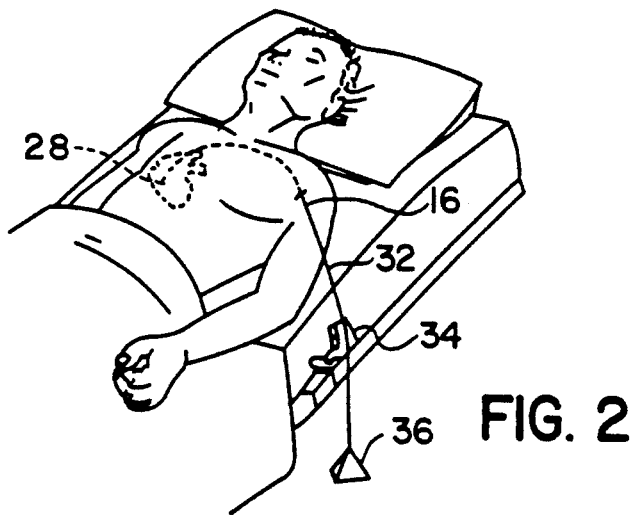
FIG. 2
FIG. 3
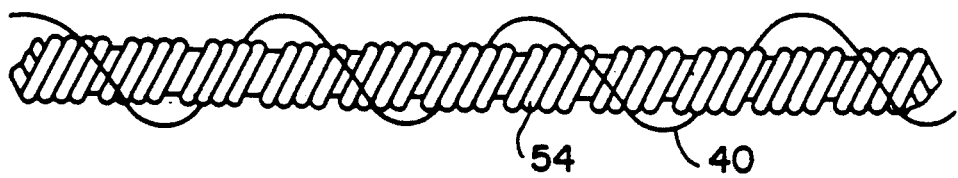

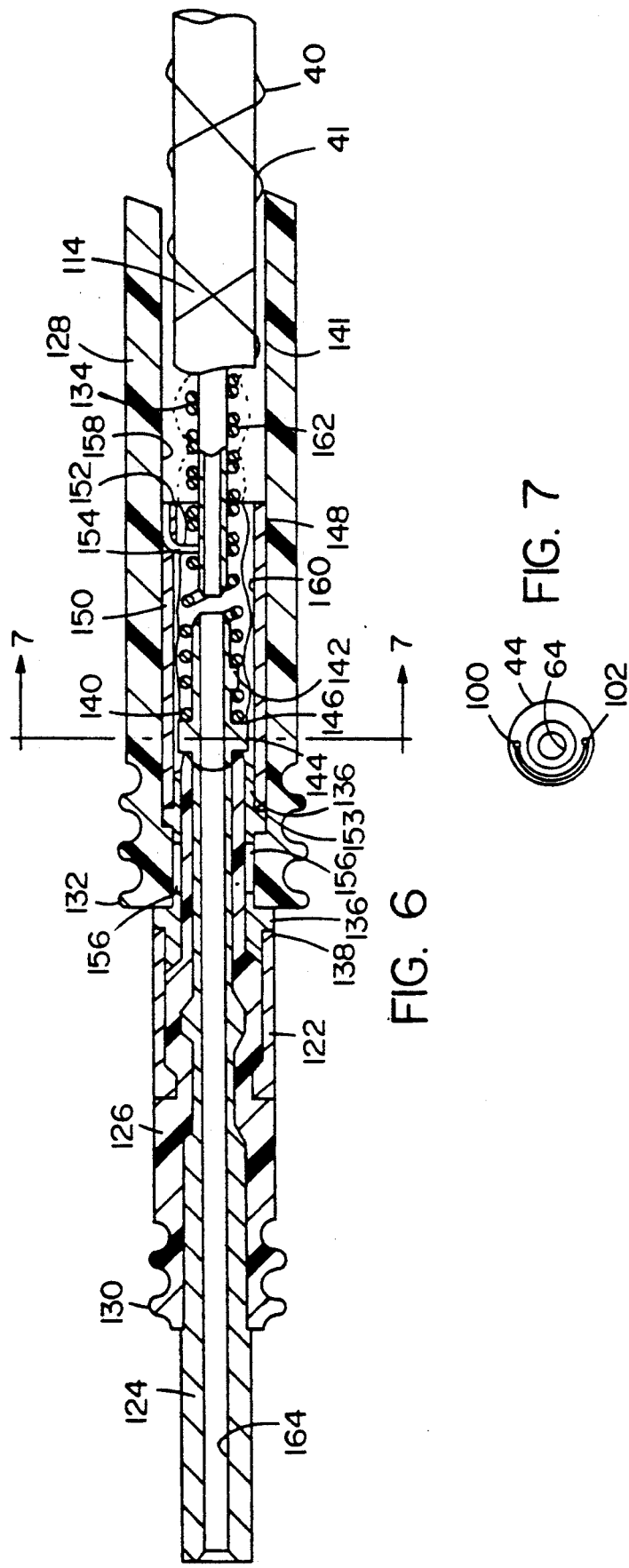

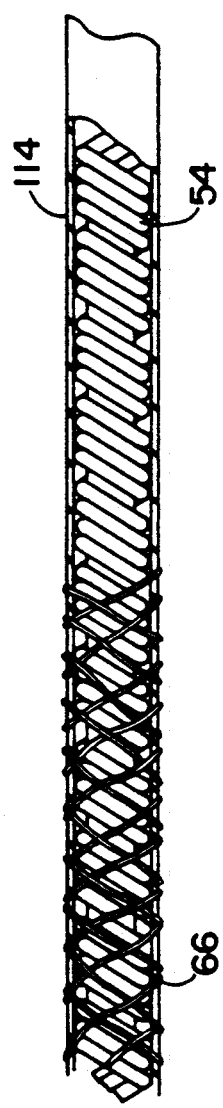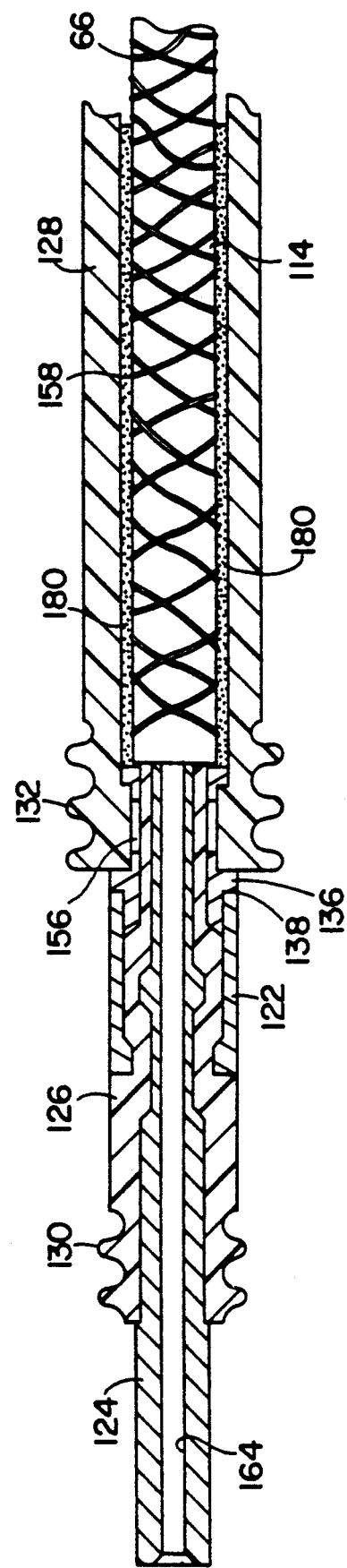

REMOVABLE ENDOCARDIAL LEAD

BACKGROUND OF THE INVENTION

1. Field of the Invention

This invention relates to coiled wire medical lead structures, such as transvenous, endocardial cardiac pacemaker and/or cardioverter/defibrillator leads. More particularly this invention relates to an improved structure for strengthening such leads to enable their intact removal by forceful traction after a period of chronic implant, specifically without the need of special lead removal devices.

2. Description of the Prior Art

Various types of transvenous pacing and cardioversion/defibrillation leads have been developed for endocardial introduction into different chambers of a patient's heart, typically the right ventricle or right atrial appendage, as well as the coronary sinus. These flexible leads usually are constructed having an outer polymeric sheath encasing one or more electrical, coiled wire conductors. One coiled wire conductor is typically attached at its distal tip to the shank portion of a tip electrode. In bipolar or multipolar leads, one or more further coiled wire conductors are provided in coaxial or co-linear relation to the first coiled wire conductor and are connected at its distal end to more proximally located, ring-shaped electrodes situated along the lead body. The proximal ends of each conductor are coupled to a connector which includes a single pin in unipolar leads and additional pins or in-line rings in bipolar and multi-polar leads.

The tip electrode is usually placed in contact with myocardial tissue by passage through a venous access, often the subclavian vein or one of its tributaries, which leads to the endocardial surface of the heart chambers. The tip electrode is held in place passively by trabeculations of myocardial tissue or actively through the use of an actively manipulated anchor or screw that penetrates the myocardium as described in U.S. Pat. Nos. 4,209,019 and 3,974,834, assigned to Medtronic, Inc. The distal ends of many available leads include flexible tines, flanges, or finger-like projections which extend radially outward and usually are molded from and are integral with the distal portion of the insulating sheath of the lead, usually proximal to the tip electrode and distal from any ring electrodes. These passive fixation mechanisms allow surrounding growth of tissue and scar in chronically implanted leads to fix the electrode tip in position in the heart and prevent dislodgement of the tip during the life of the lead.

In "acute" placement of the electrode tip, a blood clot forms about the fixation mechanism and insulating sheath (due to enzymes released as a result of irritation of the trabeculations of the myocardial tissue by the presence of the electrode tip) until scar tissue eventually forms, usually in three to six weeks. Until scar tissue develops, the fixation mechanisms described above prevent early dislodgement of the lead tip.

Although the state of the art in implanted pulse generator and endocardial lead technology has advanced considerably, endocardial leads nevertheless occasionally fail for a variety of reasons such as the following: insulation failure; sensor failure; coiled wire conductor fracture; and an increase in electrode resistance beyond a desirable level. Also, in some instances, it may be desirable to electronically stimulate different portions of the heart than are presently being stimulated with leads already in place. There are a considerable number of patients who have had one or more, and sometimes as many as four or five previously and currently used leads in their veins and heart.

The risks of leaving unusable leads in the heart and venous path include the following: an increased likelihood of infection; a potentially fatal complication which may necessitate removal of the lead; obstruction to blood flow as in "SVC syndrome"; and an increased likelihood of the formation of blood clots which may embolize to the lung and produce severe complications and even death. In addition, extra leads in the heart can interefere with cardiac valve and mechanical function. Thus, it is desirable to remove old unusable leads. Finally, the presence of unused leads in the venous pathway and inside the heart can cause considerable difficulty in the positioning and attachment of new endocardial leads in the heart.

In patients where implanted leads fails, it is desirable that they be removed. However, surgeons usually have avoided attempts to remove previously implanted leads because the risk of removing them exceeds the risk of leaving them in. Heretofore, removal techniques in the replacement surgery typically have involved applying traction to the old lead either by grasping the exposed proximal end of the lead and attempting to manually pull the lead out of the vein, or by attaching the proximal connector end to a line and weight suspended by a pulley and allowing the steady traction to gradually pull the lead free from the patient's heart over several hours to days, as herein shown in FIG. 2 and described in numerous published papers, such as "Incarceration of Transvenous Pacemaker Electrode. Removal By Traction," by A. M. Bilgutay, et al., *American Heart Journal*, Vol. 77, No. 3, pp. 377-379, March 1969.

Grasping and applying traction on the proximal ends of the chronically implanted leads results in directing pulling forces substantially along the length of the lead. These pulling forces are transmitted through the lead to its distal tip. Because of the fibrosis enveloping the electrode, substantial resistance to the pulling forces is experienced, and stress is placed on the lead as well as the heart.

As described above, endocardial lead construction typically includes a polymeric insulating sheath, within which one or more electrical, coiled wire conductors are mounted and attached to distally located electrodes and proximally located connector pins. Unfortunately, these leads have typically been constructed in such a manner which tends to make their subsequent removal difficult. When subjected to pulling forces along its length, such a lead usually disassembles. The polymeric insulating sheath can break away from the proximal and distal ends of the lead while the coiled wire conductor is stretched until it breaks or has to be cut off at the venous access site. The exposed end of a coiled wire conductor, once extended and stretched, may present the risk of cutting adjacent tissue if left in place. In such cases, only open heart surgery can fully remove the lead.

A further complication of applying direct manual pulling force to the proximal end of the lead is the avulsion of the heart, which can induce arrhythmias or even lead to death. Thus, care must be taken to observe the procedure under fluoroscopy and to avoid either breaking the lead structure or causing avulsion of the heart.

Various techniques and lead removal tools have been proposed to temporarily strengthen the lead body during the attempted removal and/or to cut away the connective tissue and, in some instances, the fixation mechanism, leaving part of it in the heart. Such tools as are disclosed in U.S. Pat. Nos. 4,988,347, 4,574,800, and 4,582,056 typically involve the use of a special stylet inserted into the lumen of the coiled wire conductor having an expandable member at its distal tip for wedging into the distal coiled wire conductor at its connection with the tip electrode shank and applying traction to the combined lead and attached wire stylet. Furthermore, it has been proposed to employ a catheter advanced over the outer sheath of the lead to sever the connective tissue adhering to the sheath along its length and at its distal tip. Other procedures include special grasping tools for grasping the lead body, as described, for example, in "Percutaneous Removal of Ventricular Pacemaker Electrodes Using a Dormier Basket," by C. J. Foster, et al., in *Int. Jr. of Cardiology*, 21 (1988) 127-134, and publications cited therein.

The procedures employing these removal tools are relatively complex and expensive and are usually resorted to only in those instances where the application of traction has proven ineffective. It is therefore desirable to provide a removable lead construction which reduces the necessity of resorting to the use of special tools or procedures.

SUMMARY OF THE INVENTION

It is therefore an object of the present invention to provide a lead body construction which enhances its chronic removability without the use of special tools or procedures, particularly in those cases where the application of chronic traction would result in the removal of the lead but for its tendency to break up in the process.

It is a further object of the present invention to provide such an enhanced removable lead construction that is simple and inexpensive to implement in existing lead bodies.

These and other objects of the invention are realized in a removable lead body construction in an elongated medical lead, such as an endocardial lead used typically for pacing or cardioversion/defibrillation.

A preferred embodiment of such removable lead includes the following:

(a) an outer insulating sheath having a relaxed predetermined length between a proximal and distal end thereof, the sheath being capable of lengthening under tension;

(b) at least one conductor positioned within said outer insulating sheath and extending between the proximal and distal ends thereof, the conductor being capable of lengthening under tension;

(c) a connector attached at the proximal end of the sheath and to the proximal end of each conductor therein for providing an electrical connection to an implanted pulse generator;

(d) at least one distal tip electrode having a normally insulated shank portion and an exposed electrode surface, and means for electrically and mechanically connecting the distal end of the conductor to the electrically insulated portion of the electrode; and (e) wherein the improvement in the lead body construction comprises one or more normally relaxed, non-extensible filaments loosely contained within the insulating sheath and having proximal and distal ends mechanically coupled to the connector and the normally insulated portion of the electrode, respectively, for restraining the stretching of the lead body to a stretched length exceeding the relaxed predetermined length by an amount sufficient to allow the lead to be stretched without breaking in its normal usage and during removal by traction.

In further embodiments of the invention, the filament(s) preferably take the form of Dacron ® polyester yarn or cord having a size of approximately 2,600 denier that are mechanically attached to the connector and the electrode shank by passing the ends of the filament through holes therein and tying the ends off and either wound loosely about a coiled wire conductor or extended through the lumen of the coiled wire conductor.

In further embodiments of the present invention, it is contemplated that the filaments may be replaced by a loosely woven fabric sheath formed in a tubular shape and fitted in the space between the outer sheath and the coiled wire conductor or between the outer sheath and the inner sheath surrounding one of the coiled wire conductors. In this latter embodiment, the ends of the sheath are mechanically attached to the connector and the electrode assembly such that as the loosely woven fibers are stretched, they tighten against a sheath surrounding the conductor or the conductor itself, and thus grip the insulation or the coiled wire conductor through the length of the lead body, substantially increasing its tensile pull strength.

It is also contemplated that the filament(s) or woven sheath may be embedded within or on the interior surface of the outer insulating sheath on an inner insulating sheath of a bipolar or multipolar lead.

BRIEF DESCRIPTION OF THE DRAWINGS

These and other objects and advantages of the present invention will become apparent from the following drawings of the preferred embodiments thereof, which drawings are not necessarily drawn to actual scale, wherein like components or structures are identified by like numbers, and in which:

FIG. 1 is a side elevation view of a typical unipolar pacing lead within which the present invention may be implemented;

FIG. 2 depicts the removal from the heart of an electrical pacemaker lead implanted with its distal tip electrode situated in the right ventricle through applied traction;

FIG. 3 illustrates one slack filament wound loosely about a coiled wire conductor of the type employed in the lead of FIG. 1;

FIG. 6 depicts in partial cross-sectional view the connection of the filament of FIG. 3 to the proximal connector assembly of a lead of the type depicted in FIG. 1;

FIG. 7 is a sectional view of a portion of the connector of FIG. 6 illustrating one mode of connection of the filament;

FIG. 8 depicts in partial side elevation view the arrangement of a loosely wound coaxial, tubular reinforcing sheath arranged about a section of the coil of the lead of FIG. 1;

FIG. 10 depicts in partial cross-sectional view of the mechanical connection of the proximal end of the tubular sheath of FIG. 7 to the proximal connector assembly of a lead of the type depicted in FIG. 1.

DETAILED DESCRIPTION OF THE PREFERRED EMBODIMENTS OF THE INVENTION

Figure 4:
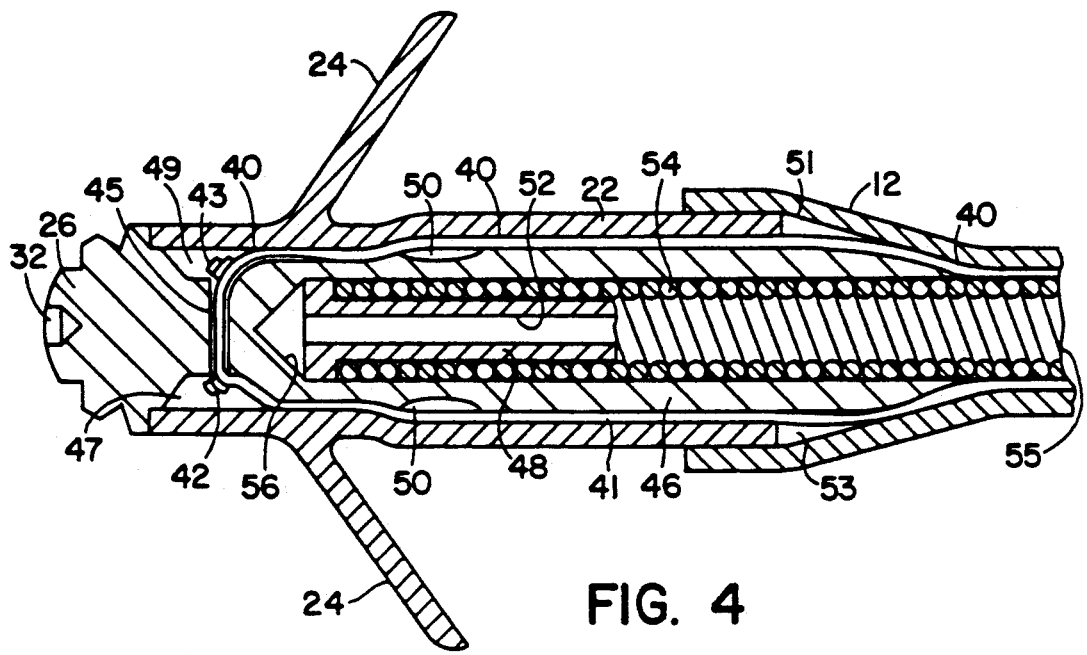
FIG. 4 depicts in partial cross-sectional view of one embodiment of the connection of the distal end of the filament of FIG. 3 to the shank of the tip electrode of a lead of the type depicted in FIG. 1.

FIG. 1 shows a side plan view of a simple, unipolar, endocardial pacing lead according to the present invention. The lead is provided with an elongated lead body 10 which is covered with an insulation sheath 12, which may be fabricated of silicone rubber, polyurethane or other suitable plastic. At the proximal end of lead body 10 is connector assembly 16, which is provided with sealing rings 18 and which carries connector pin 20. Connector assembly 16 may be constructed using techniques known to the art, and may be fabricated of silicone rubber, polyurethane or other suitable plastic. Connector pin 20 may be fabricated of stainless steel or other conductive material. At the distal end of lead body 10 is electrode 26 which is discussed in more detail below. Immediately proximal to the exposed portion of electrode 26 is tine sheath 22 which bears four tines 24, of which three are visible. Tines 24 engage with heart tissue and urge electrode 26 into contact with the endocardium, in a direction parallel to the lead axis. Tines 24 are more fully described in U.S. Pat. No. 3,902,501, issued to Citron et al, incorporated herein by reference. Slideably mounted around lead body 10 is fixation sleeve 14, which serves to stabilize the lead at the site of venous insertion. Sleeve 14 is more fully described in commonly assigned U.S. Pat. No. 4,437,475.

Turning to FIG. 2, a cardiac pacing lead, generally designated as 10 in FIG. 1, is illustrated such that its implanted electrode 26 is fixed at its most distal tip by tissue and/or trabeculae in the right ventricle of the illustrated heart 28 of the reclining patient. It is to be understood that the implanted condition generally illustrated in the drawing includes having a substantial length of the cardiac pacing lead 10 implanted within an appropriate vein (not shown) of the patient, while the proximal connector pin 20 of the lead 10 is accessible for connection to a pacemaker in accordance with generally well-known structures and procedures.

In order to remove a chronically implanted and fibrosed-in lead, steady traction is employed in the manner shown in FIG. 2. The proximal connector 16 and connector pin 20 of the lead 10 is exposed by an incision and attached to a line 32. The line 32 is suspended over a shoulder level pulley 34 and attached to a weight 36, e.g., 1 to 10 lbs. Normally the application of slow steady traction loosens the attachment of the distal electrode and fixation mechanism of the lead 10. But prior to resorting to such traction, the physician may attempt to manually withdraw the lead and apply even greater pulling force to it, which may damage the lead as described above.

In accordance with one embodiment of the present invention, the lead body is strengthened by the inclusion of one or more slack filaments 40 within the insulating sheath 12 of the lead depicted in FIGS. 1 and 2 and wound loosely about the coil 54 of at least one of the coiled wire conductors in either a unipolar embodiment as depicted in FIG. 1 or in bipolar and multipolar embodiments thereof. In FIG. 3, the slack, loosely wound, filament 40 is shown in a partial schematic view of its orientation to the coiled wire conductor 54 merely to illustrate that the filament or filaments are intentionally loosely wound around either the inner or outer coiled wire conductor to allow the lead to possess its normal flexibility and springiness in its normal intended usage in the implantation depicted, for example, in FIG. 2.

The filament 40 extends between the connector 16 at the proximal end of the lead 10 and the tip electrode 26 at the distal end of the lead depicted in FIG. 1 and within the insulating sheath 12. When the lead body is stretched to approximately 110% to 120% of its normal relaxed length, the filament draws tight against the coiled wire conductors and prevents further stretching of the lead body, unless it is subjected to a pulling force far in excess of most manual traction situations, such as more than 20–30 lbs. of axially applied force.

Preferably, filaments 40 are lengths of Dacron woven yarn of relatively small cross-sectional area. A yarn, as opposed to a monofilament, is preferred that possesses the requisite strength, will flatten out in a constrained space and is not susceptible to stretching, but will instead break at the desired 20 lbs. traction applied to the lead body.

Figure 5:
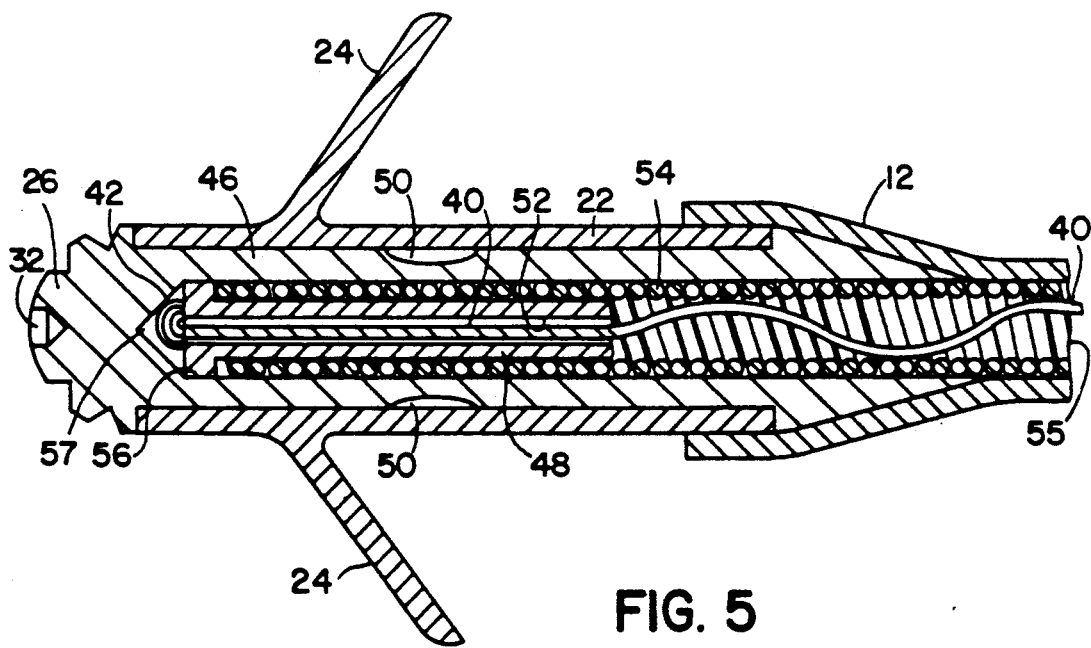
FIG. 5 depicts in partial cross-sectional view a further attachment mechanism for the distal end of the filament of FIG. 3 to the shank of the tip electrode of a lead of the type depicted in FIG. 1.

Turning now to FIGS. 4 and 5, alternative attachment mechanisms are depicted for attaching one or more filaments 40 to the shank 46 of the distal electrode 26. The distal electrode 26 preferably takes the form of that electrode shown in U.S. Pat. No. 4,502,492 incorporated herein by reference.

FIG. 4 shows a cross-sectional view of the distal end of the lead of FIG. 1. In this view, electrode 26 is seen to be provided with an elongated, proximally extending tubular shank 46 which has a central lumen 56. Mounted within lumen 56 are swaging pin 48 and coiled conductor 54. Crimps 50 maintain coiled conductor 54 tightly fixed between swaging pin 48 and tubular portion 46 of electrode 26. This structure provides mechanical and electrical coupling of conductor 54 to electrode 26. Coiled conductor 54 extends proximally within insulating sheath 12 to the proximal end of the lead and is coupled to connector pin 20 (FIG. 1). Swaging pin 48 is provided with a central lumen 52 into which a stylet may be inserted. Coiled conductor 54 may be fabricated of MP35N alloy or other suitable conductive material, and is preferably a multifilar coil as shown in FIG. 3. Swaging pin 48 may be fabricated of stainless steel or other appropriate metal. Electrode 26 is preferably constructed of or provided with a coating of platinum or of a platinum alloy, but may also be constructed of titanium, rhodium, iridium, or alloys thereof.

In order to accommodate the filaments 40, 41, the distal end of the lead of FIGS. 1 and 2 as described in the aforementioned '492 patent is modified as depicted in FIG. 4 to provide a hole 45 through the tubular shank portion 46 extending between recesses 47, 49 distal to the crimps 50. The filament ends 42, 43 of filaments 40, 41 are threaded in opposite directions through hole 45 and tied off and fitted within the recesses 47 and 49 of the tubular portion 46. The recesses 47, 49 and hole 45 may or may not be filled with epoxy cement to stabilize the filaments 40, 41 in hole 45 and recesses 47 and 49.

The filaments 40, 41 extends along the outer surface of the tubular shank portion 46 and within the tine sheath 22 and through grooves cut in the shank ridge at 51, 53 whereafter it is wound loosely about the coil 54 as shown in FIG. 3 through the length of the lead body. A single filament could be employed in the same fashion as shown in the partial cross-sectional view of FIG. 4.

Turning now to FIG. 5, a further embodiment of the connection of the distal end of the filament with the shank of the connector end is depicted. In FIG. 5, the filament 40 extends through the lumen 55 of the coiled wire conductor 54 throughout its length and through the lumen 52 of the swaging pin 48. In assembly, the filament is threaded through the lumen 52 and knotted at its distal end 42. A dab of epoxy may be applied to the knot 42. The coiled wire conductor 54 is slipped over the outer surface of the swaging pin 48, and the assembly is inserted into the central lumen 56 of the elongated shank tubular portion 46 to locate the knot 42 in the end 57 of lumen 56. The mechanical and electrical attachment is completed in the manner described above by swaging at points 50. In this embodiment, the filament extends loosely down the lumen of the coiled wire conductor to the connector where it is attached thereto.

Turning now to FIGS. 6 and 7, the connector end of the lead of FIGS. 1 and 2 is depicted in partial cross-section to illustrate the fashion in which the proximal end of the filaments 40, 41 may be attached thereto. FIG. 6 is a modification of FIG. 2 of U.S. Pat. No. 4,944,088 incorporated herein by reference in its entirety. Basically, the filaments 40, 41 actually constitute a single length of filament which are passed through holes 100, 102, in a ring element 144 and wound about the inner coil 134 or sheath 114 to extend between the coil 134 and the inner sheath 114 or the outer sheath 128 through the length of the lead body. In the bipolar lead embodiments, the filaments 40, 41 may be loosely wound about either the inner sheath or coil and connected at the distal tip electrode in the fashion depicted, e.g., in FIG. 4 as described above. It will be understood that the filaments 40, 41 could be threaded through a similar connection in a unipolar connector and with or without the inner sheath 114.

Turning now specifically to FIG. 6, it shows a cross-sectional view of the proximal portion of a bipolar connector assembly showing the interconnection of the multiconductor coil 134 with the other components of the connector assembly. Multiconductor coil 134 includes a first coil conductor coupled to connector pin 124 and a second coil conductor electrically coupled to ring member 122.

The connector assembly is fabricated by first laser welding ring member 122 to cylindrical member 136 by means of a circumferential laser weld at 138 to form a connector ring assembly. Assembled ring member 122 and cylindrical member 136 are assembled over connector pin 124, placed into a mold, and insulative sleeve 126 is then injection molded between them. This process is disclosed in more detail in Hess U.S. Pat. No. 4,572,605, and incorporated herein by reference in its entirety.

The complete assembly of connector pin 124, insulative sleeve 126, ring member 122 and tubular member 136 is then coupled to one conductor 140 of multiconductor coil 134. Conductor 140 is screwed onto the distal end of connector pin 124, with protrusion 142 acting as a screw thread. Conductor 140 is screwed onto connector pin 124 until its proximal end abuts against circular flange 144. Conductor 140 is then coupled to circular flange 144 at 146 by means of a spot laser weld. The spacing of intermediate circular flange 144 and protrusion 142 allows for a limited amount of strain relief immediately distal to the spot laser weld at 146.

Tubular extension 148, which takes the form of a cylinder having an extended longitudinal slot 150 is then slid over the distal end of cylindrical member 136 and coupled to it by means of a circumferential laser weld at 153. A shallow grooved section 152, having a groove that corresponds generally to the size of conductor 154, is located at the proximal end of slot 150 in tubular extension 148. Conductor 154 is stripped of insulation and laid lengthwise in the grooved area 152, and laser welded to extension 148. Following this step, insulative sleeve 128 is slid over extension 148 and over cylindrical member 136. Member 136 is provided with a cross bore 156, which may be filled with medical adhesive, thereby bonding insulative sleeve 128 to insulative sleeve 126.

Finally, the entire assembly is backfilled with adhesive injected between insulative sheath 114 and insulative sleeve 128, filling the area between insulative sleeve 128 and sheath 114, as well as the lumen 158 of sleeve 128 and the lumen 160 of tubular extension 148. This serves to bond the components of the connector assembly to one another and to insulative sleeve 128 and to electrically insulate the conductor 140 and connector pin 124 from the conductor 154. For the sake of clarity, the backfilled adhesive is not shown in this illustration. Mounted within multiconductor coil 134 is a Teflon ® plastic liner 162, which serves as a passageway for a stylet. The internal lumen of liner 62 is aligned with the internal bore 164 of connector pin 124.

As stated hereinbefore, the filaments 40, 41 in this embodiment actually comprise a single filament threaded through holes 100, 102 shown in the cross-sectional view of FIG. 7 extending through the circular flange 144 in and out of holes 100 and 102. It will be appreciated that a single filament could be passed through the holes 100, 102 and tied off, rather than looped back as the second filament as shown in FIG. 6. It will also be appreciated that the filament or filaments may be looped through holes in other parts of the proximal lead assembly of FIG. 6, such as holes passing through the sidewalls of tubular extension 148.

The connector end as described above in conjunction with FIGS. 6 and 7 involves the implementation of the invention in the context of the above-incorporated '088 patent where the individual conductors of multiconductor coil 134 are separately insulated and connected to connector pin 124 and ring 122. It will be understood that the same attachment of the filaments 40, 41 through the flange 144 may be accomplished in less complex connectors where all of the multifilar, coaxial conductors are electrically and mechanically connected to the connector pin 124 and the tubular extension 148 and its attachment to one of the conductors of coil 134 is eliminated. In such embodiments, the flange 144 is present and functions as described above, but it may have a larger relative diameter than illustrated in FIG. 6.

In the embodiment of FIG. 5, where the filament 40 extends through the lumen 55 of the coiled wire conductor 54, the proximal end of the filament 40 would be drawn through a spaced apart turn of the multifilar coil 134 at its juncture with the distal end of the connector pin 124 and attached in the same fashion as depicted in FIGS. 6 and 7 and described above. Other mechanisms for attaching the proximal and distal ends of the filament will be apparent to those of skill in the art and depend upon particular attachment configurations of existing and future lead designs.

Turning now to FIG. 8, it depicts in partial side elevation view, the arrangement of a loosely wound, coaxial, tubular reinforcing sheath 66 fitted over the coiled wire conductor 54 or the insulating sheath 114. It will be appreciated that the loosely wound tubular sheath is an extension of the number of filaments from one or two as previously described but would employ a Dacron fabric having individual webs of a greater width than thickness and which would be capable of being stretched a certain amount until its shrinking inner diameter would firmly grip the outer surface of the coiled wire conductor 54 or the insulating sheath 114. Thus, the reinforcing sheath 66 would operate in the fashion of a Chinese finger pull toy on the underlying coil or insulating sheath.

Figure 9:
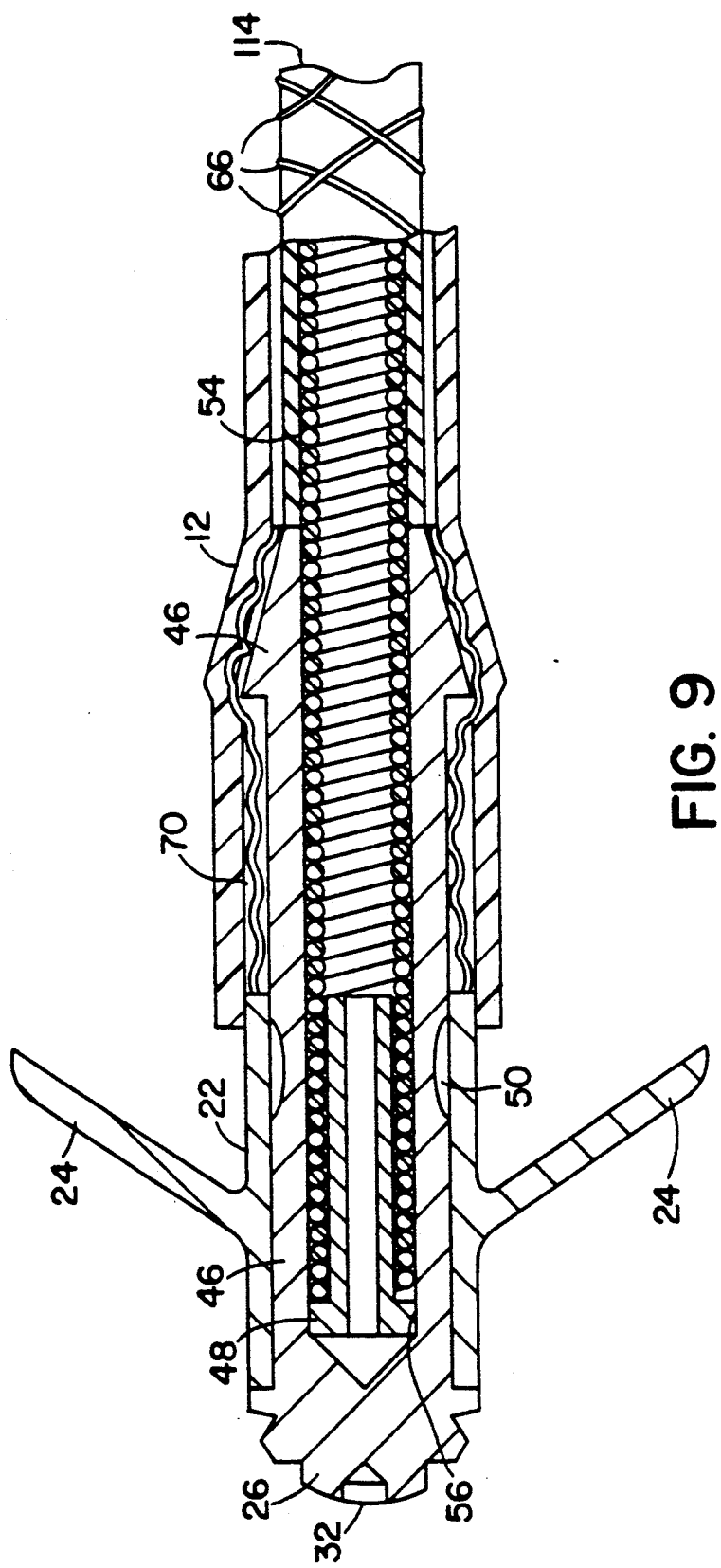
FIG. 9 depicts in partial cross-sectional view the connection of the distal end of the sheath of FIG. 7 to the shank of the tip electrode of a lead of the type depicted in FIG. 1.

Turning now to FIG. 9, a cross-sectional sideview of a distal tip similar to the distal tips depicted in FIGS. 4 and 5 illustrates one manner of attaching the loosely woven, criss-crossed or braided reinforcing sheath 66. In this embodiment, the loosely woven sheath 66 is fitted over the inner insulating sheath 114 and inside the outer insulating sheath 12. The distal end of the tubular reinforcing sheath 66 is fitted over the flange of the tubular shank 46 which itself forms the distal electrode 26 as described above. The distal end of the tubular sheath 66 is pressed against the periphery of the shank 46 by a layer of heat shrink tubing 70 which extends over a predetermined length of the distal end of the sheath 66 after it is itself fitted over the shank 46 and heat shrunk in place. Thereafter, the outer insulating sheath 12 is placed over the assembly to further strengthen and insulate the lead body.

The connection of the loosely woven, reinforcing sheath 66 at the proximal, connector end of the lead of FIGS. 8 and 9 is depicted schematically in FIG. 10. FIG. 10 generally corresponds in structure to FIG. 6 except that conductive tube 154 is not present (as suggested above) and inner sheath 114 extends over the inner conductor coil and its attachment to connector pin 124. The loosely woven sheath 66 extends over inner sheath 114 and inside outer connector sheath 128. The space 180 within the outer connector sheath 128 would be filled with adhesive to fix the components together when traction is placed on the lead as described above. The adhesion of the sheath 66 to the connector structure may also be achieved through other means, including heat shrink wrap tubing as described in connection with FIG. 9.

In a still further embodiment, it is contemplated that the reinforcing sheath 66 or the filaments 40, 41 may be embedded on a surface of or within an insulating sheath through the length of the lead body such that the sheath may be stretched to only a predetermined stretched length exceeding its normal relaxed length during application of traction forces.

Many other benefits also follow from the present invention. For example, the novel lead body reinforcement structure described herein also provides additional tensile support at the distal end of the lead body, which can be particularly useful for the physician who encounters, during a lead replacement procedure, an occasionally stubborn pacemaker connector block/pacing lead connector which requires significant pulling force to separate the lead from the pacemaker. Finally, the limited extensibility provided by claimed lead body reinforcement structure also provides benefit to the patient who may encounter a physically traumatic event, such as a fall, or an automobile accident, to the extent that the lead body can accommodate whatever stress may be exerted upon the lead body by allowing moderate lead body stretching without incurring lead damage or dislodgement.

Although the particular embodiments disclosed in this application take the form of cardiac pacing leads, the inventions disclosed hereon are believed equally applicable to medical electrical leads in general.

What is claimed is:

1. In an elongated electrical medical lead for use with a pulse generator to be implanted within a human body,
   (a) said lead having a proximal and distal lead end and further comprising:
      (1) an outer insulating sheath having a relaxed predetermined sheath length between a proximal and distal sheath end thereof, said sheath being capable of lengthening under tension;
      (2) at least one conductor positioned within said outer insulating sheath and extending between said proximal and distal sheath ends thereof, each of said at least one conductor having a relaxed predetermined conductor length between a proximal and distal conductor end thereof, and each of said at least one conductor being capable of lengthening under tension;
      (3) a connector interconnecting said proximal sheath end with said proximal conductor end of each of said at least one conductor therein, said connector for providing an electrical connection to said implanted pulse generator;
      (4) at least one tip electrode disposed adjacent said distal sheath end of said lead, each of said at least one electrode having a normally electrically insulated shank portion and an exposed electrode surface; and
      (5) means for electrically and mechanically connecting said distal conductor end of each of said at least one conductor to said electrically insulated shank portion of said electrode;
   (b) wherein the improvement in said lead body construction comprises:
   lead body strengthening means permanently attached at said proximal and distal lead ends and extending therebetween for allowing said lead body insulating sheath and each of said at least one conductor to be stretched only to an extended predetermined length exceeding said relaxed predetermined length as long as applied tension does not exceed the tensile strength of said lead body strengthening means.

2. The elongated electrical medical lead of claim 1, wherein:
   said lead body strengthening means does not restrain the stretching and lengthening of said lead body insulating sheath and conductor between said relaxed and extended predetermined lengths.

3. The elongated electrical medical lead of claim 1, wherein:
   said lead body strengthening means further comprises one or more normally relaxed, nonextensible filaments loosely contained within said insulating sheath and having proximal and distal filament ends mechanically coupled to said connector and said normally insulated shank portion of said electrode, respectively, said filaments for restraining the stretching of said lead body to a stretched length exceeding said relaxed predetermined length by an amount sufficient to allow said lead to be stretched without breaking in its normal usage and during removal by traction.

4. The elongated electrical medical lead of claim 3, wherein:
   (a) each of said at least one conductor comprises a coiled wire conductor; and
   (b) said one or more filaments comprise a polyester yarn loosely wound around the outer diameter of said coiled wire conductor, said yarn being mechanically attached to said connector and said normally insulated shank portion of said electrode.

5. The elongated electrical medical lead of claim 3, wherein:
   (a) said conductor comprises a coiled wire conductor;
   (b) said one or more filaments comprise a loosely woven fabric sheath formed in a tubular shape and fitted loosely around said coiled wire conductor in its relaxed condition; and
   (c) said lead body construction further comprises means for mechanically connecting said loosely woven fabric sheath to said connector and said normally insulated shank portion of said electrode.

6. In a transvenous, electrical medical lead for use with a pulse generator to be implanted within the human body,
   (a) said lead having a proximal and distal lead end and further comprising:
      (1) an outer insulating sheath having a relaxed predetermined sheath length between a proximal and distal sheath end thereof, said sheath being capable of lengthening under tension;
      (2) at least one conductor positioned within said outer insulating sheath and extending between said proximal and distal sheath ends thereof, each of said at least one conductor having a relaxed predetermined conductor length between a proximal and distal conductor end thereof, and each of said at least one conductor being capable of lengthening under tension;
      (3) a connector interconnecting said proximal sheath end with said proximal conductor end of each of said at least one conductor therein, said connector for providing an electrical connection to said implanted pulse generator;
      (4) at least one tip electrode disposed adjacent said distal sheath end of said lead, each of said at least one electrode having a normally electrically insulated shank portion and an exposed electrode surface; and
      (5) means for electrically and mechanically connecting said distal conductor end of each of said at least one conductor to said electrically insulated shank portion of said electrode;
   (b) wherein the improvement comprises:
   means connected to said connector and said distal tip electrode for allowing said lead body extending therebetween to be stretched to a stretched length exceeding its normal relaxed length and for preventing the extension of said lead body beyond said stretched length during the application of traction forces thereto until a predetermined traction force is exceeded.

7. The lead of claim 6, wherein:
said lead body strengthening means does not restrain the stretching and lengthening of said lead body insulating sheath and conductor between said relaxed and extended predetermined lengths.

8. The elongated electrical medical lead of claim 1, wherein:
said lead body strengthening means further comprises one or more normally relaxed, nonextensible filaments loosely contained within said insulating sheath and having proximal and distal filament ends mechanically coupled to said connector and said normally insulated shank portion of said electrode, respectively, said filaments for restraining the stretching of said lead body to a stretched length exceeding said relaxed predetermined length by an amount sufficient to allow said lead to be stretched without breaking in its normal usage and during removal by traction.

9. The elongated electrical medical lead of claim 8, wherein:
   (a) each of said at least one conductor comprises a coiled wire conductor; and
   (b) said one or more filaments comprise a polyester yarn loosely wound around the outer diameter of said coiled wire conductor, said yarn being mechanically attached to said connector and said normally insulated shank portion of said electrode.

10. The elongated electrical medical lead of claim 8, wherein:
   (a) said conductor comprises a coiled wire conductor;
   (b) said one or more filaments comprise a loosely woven fabric sheath formed in a tubular shape and fitted loosely around said coiled wire conductor in its relaxed condition; and
   (c) said lead body construction further comprises means for mechanically connecting said loosely woven fabric sheath to said connector and said normally insulated shank portion of said electrode.

* * * * *